(12) United States Patent
Swinger

(10) Patent No.: US 8,342,688 B1
(45) Date of Patent: Jan. 1, 2013

(54) MULTIFOCAL CAPABLE OPHTHALMIC ABERROMETER

(76) Inventor: Casimir Andrew Swinger, New York, NY (US)

( * ) Notice: Subject to any disclaimer, the term of this patent is extended or adjusted under 35 U.S.C. 154(b) by 109 days.

(21) Appl. No.: 12/815,107

(22) Filed: Jun. 14, 2010

Related U.S. Application Data

(60) Provisional application No. 61/268,711, filed on Jun. 15, 2009.

(51) Int. Cl.
*A61B 3/10* (2006.01)
*A61B 3/04* (2006.01)
(52) U.S. Cl. .................. 351/221; 351/228; 351/205
(58) Field of Classification Search .......... 351/200–246
See application file for complete search history.

(56) References Cited

U.S. PATENT DOCUMENTS

| | | | |
|---|---|---|---|
| 6,270,221 B1 * | 8/2001 | Liang et al. .................. 351/221 |
| 6,325,792 B1 | 12/2001 | Swinger et al. | |
| 6,382,795 B1 | 5/2002 | Lai | |
| 6,406,146 B1 * | 6/2002 | Lai .............................. 351/206 |
| 6,460,997 B1 * | 10/2002 | Frey et al. ..................... 351/211 |
| 6,575,572 B2 * | 6/2003 | Lai et al. ...................... 351/211 |
| 2005/0241653 A1 | 11/2005 | Van Heugten et al. | |
| 2005/0243276 A1 | 11/2005 | Van Heugten et al. | |

\* cited by examiner

*Primary Examiner* — Mohammed Hasan

(57) ABSTRACT

A multifocal capable ophthalmic aberrometer has an afocal relay defining an optical axis, an object plane, and an image plane. The image plane is conjugated to the object plane. A probe beam is projected along the optical axis and is propagated toward the object plane. Reflection of the probe beam from a subject eye located at the object plane generates a wavefront emerging from the object plane. A Hartmann-Shack sensor positioned at the image plane and produces an image of Hartmann-Shack spots of the wavefront. A control electronics acquires the images of the Hartmann-Shack spots in a single measurement. A processing electronics calculates an optical power map of the subject eye with respect to a center of the wavefront and averages the optical power map over the images.

20 Claims, 4 Drawing Sheets

MULTIFOCAL CAPABLE OPHTHALMIC ABERROMETER

This application takes benefit of Provisional Application 61/268,711, filed Jun. 15, 2009. The disclosure of that application is incorporated herein by reference.

TECHNICAL FIELD

The present invention relates to an ophthalmic aberrometer attachable to an ophthalmic microscope and capable of measuring a subject's eye implanted with a multifocal intraocular lens (multifocal IOL). In particular, the present invention relates to a multifocal capable aberrometer that is attachable to a microscope and configured for intraoperative use in cataract and corneal surgery.

BACKGROUND

Multifocal IOLs are an increasingly popular solution for simultaneous correction of both distance refractive error and presbyopia. Multifocal intraocular lenses are commonly known as premium IOLs. Conventional autorefractors and wavefront aberrometers are, however, not designed for measuring multifocal optics, and they typically cannot obtain a meaningful or accurate measurement of a subject's eye implanted with a multifocal IOL.

On the other hand, there is a need for intraoperative and postoperative measurement of eyes undergoing or having undergone cataract surgery and implanted with multifocal IOLs. During cataract surgery with implantation of a premium multifocal IOL, the surgeon may want to measure the IOL's performance such that any correction or adjustment can be done before the conclusion of the surgical procedure. For example, residual astigmatism is common in cataract patients and reduces the benefits of a premium IOL. Should residual astigmatism be detected in an intraoperative measurement, the surgeon can minimize it by readjusting the orientation of a toric IOL or by performing, for example, a technique such as one or more limbal relaxing incisions.

An autorefractors determines the refractive power of an eye over a small optical zone (typically only up to 3 mm in diameter) at the center of the pupil. Commonly, an autorefractor measures the refractive power at a small number of predetermined points (typically 4 points) to calculate 3 parameters of a subject's eye: 1) the spherical refractive error; 2) the magnitude of the astigmatism; and 3) the axis of the astigmatism. Obviously, an autorefractor is not capable of measuring a multifocal lens that has two or more spherical focal powers.

An ophthalmic aberrometer determines the refractive power of an eye by fitting a smooth and continuous wavefront over the entire pupil. Optical power interruption or discontinuities are not resolvable should the measurement data points have a spatial separation comparable to or bigger than the feature of the interruption, e.g., annular rings in a multifocal IOL. Optical power interruption is removed, for example, in the process of wavefront reconstruction with a relatively small number of mathematical terms, such as Zernike or Fourier coefficients. Consequently, a conventional wavefront aberrometer is not capable of measuring a multifocal lens with a sharp change in the spatial profile of optical powers.

Ophthalmic aberrometers and surgical microscopes are both commonly used in corneal and cataract surgery and are typically standalone instruments. Patients and surgeons, in light of recent advancements in cataract surgery such as the use of intraocular lenses for the correction of astigmatism (toric IOLs) and multifocal lenses for correction of both distance and near vision (presbyopia), could benefit from the ability of making intraoperative wavefront measurements. It thus calls for a need to attach an ophthalmic aberrometer onto an ophthalmic microscope.

A standalone ophthalmic aberrometer has its own positioning mechanism to align the instrument axis with the subject eye's visual axis, and thus it is typically too heavy and too big to attach onto a surgical microscope. Also, a standalone ophthalmic aberrometer typically has a short working distance in the range of 30-50 mm, while a surgical microscope typically has a working distance of 200 mm. A short working distance makes it easier for an ophthalmic aberrometer to have a larger measurement range of defocused power. On the other hand, a longer working distance is necessary for a surgeon to perform eye surgery. Therefore, there is a need to redesign the ophthalmic aberrometer in order to be attachable onto a surgical microscope and allow measurement of eyes not only with monofocal IOLs but also multifocal IOLs.

In addition, it is highly desirable for a surgeon to conduct precise microsurgery like cataract surgery with the best optics afforded by the microscope being used. It is thus preferable that the ophthalmic aberrometer shall not interfere in any way with either the working space or the image quality of the microscope.

Another concern for intraoperative wavefront measurement is confirmation of the status of the cornea at the time of the wavefront measurement as the corneal shape is a major factor in the total wavefront error of the eye. Factors, such as the intraocular pressure for instance, may affect the radius/radii of curvature of the cornea. Confirmation of the residual refractive error of the eye at the conclusion of surgery is dependent on the power of the lens implanted and the corneal curvature. Should the corneal curvature(s) not be as they were preoperatively or predicted/estimated to be postoperatively, the surgeon could obtain a less than accurate measurement of the refractive status of the eye during surgery when decisions regarding subsequent interaction, such as lens exchange or limbal relaxing incisions would be made, thereby reducing the efficacy of the intraoperative aberrometer and the final clinical result for the patient. Thus, in the intraoperative measurement of wavefront power, a concurrent measurement of corneal keratometry would be helpful to detect any induced corneal power change in the cornea, such as might be caused by failure to restore the eye to normal intraocular pressure and thus to improve the accuracy of the wavefront measurement or take the altered corneal power into consideration.

We refer to the following patents:
U.S. Pat. No. 6,382,795 May 7, 2002 M. Lai Method and apparatus for measuring refractive errors of an eye
U.S. Pat. No. 6,406,146 Jun. 18, 2002 M. Lai Wavefront refractor simultaneously recording two Hartmann-Shack images
U.S. Pat. No. 6,575,572 Jun. 10, 2003 M. Lai, et al Method and apparatus for measuring optical aberration of human eye
US2005/0241653 Nov. 3, 2005 Van Heugten et al Integrated surgical microscope and wavefront sensor

SUMMARY

The present invention contemplates a new and improved wavefront aberrometer capable of measuring astigmatism and optical power of a subject's eye implanted with a multifocal IOL.

The present invention also contemplates to implement the multifocal measurement into a Hartmann-Shack wavefront aberrometer such as to extend the usefulness of the wavefront aberrometer. The present invention further contemplates to measure accurately the optical power distribution by acquiring a significantly large number of data points and by applying a technique of data averaging but not profile fitting.

Therefore, a first objective of the invention is a wavefront aberrometer that is capable of measuring a subject's eye that has been implanted with a multifocal IOL. A second objective of the invention is a wavefront aberrometer that enables intraoperative application during cataract surgery. A third objective of the invention is a wavefront aberrometer that adapts and extends the usefulness of the popular Hartmann-Shack wavefront aberrometer. These and other objectives of the invention will become more apparent in the following drawings, detailed description, and claims.

In a co-pending patent application, the present invention contemplates a new and improved wavefront aberrometer attachable to an ophthalmic microscope. The present invention also contemplates to implement a long working distance and a large measurement range into the wavefront aberrometer. The present invention further contemplates to make it quick and easy to insert the wavefront aberrometer for intraoperative use and to move it away from the working space of the ophthalmic microscope when not being used. The present invention still further contemplates implementation of a keratometry measurement to monitor the corneal status at the time of the wavefront power measurement, as this allows the surgeon to ascertain that the corneal curvature(s) are at or near their preoperative value(s), or any value based upon the individual surgeon's technique and experience prior to making corneal relaxing incisions to correct astigmatism or making adjustments to (or exchange of) the intraocular lens based on the aberrometer reading.

Therefore, a first objective of the invention is a wavefront aberrometer that is attachable onto a microscope for intraoperative measurement during corneal and cataract surgery. A second objective of the invention is a wavefront aberrometer that is attachable onto a slit lamp microscope to provide general wavefront and refraction measurements. These and other objectives of the invention will become more apparent in the following drawings, detailed description, and claims.

DETAILED DESCRIPTION

Figure 1:
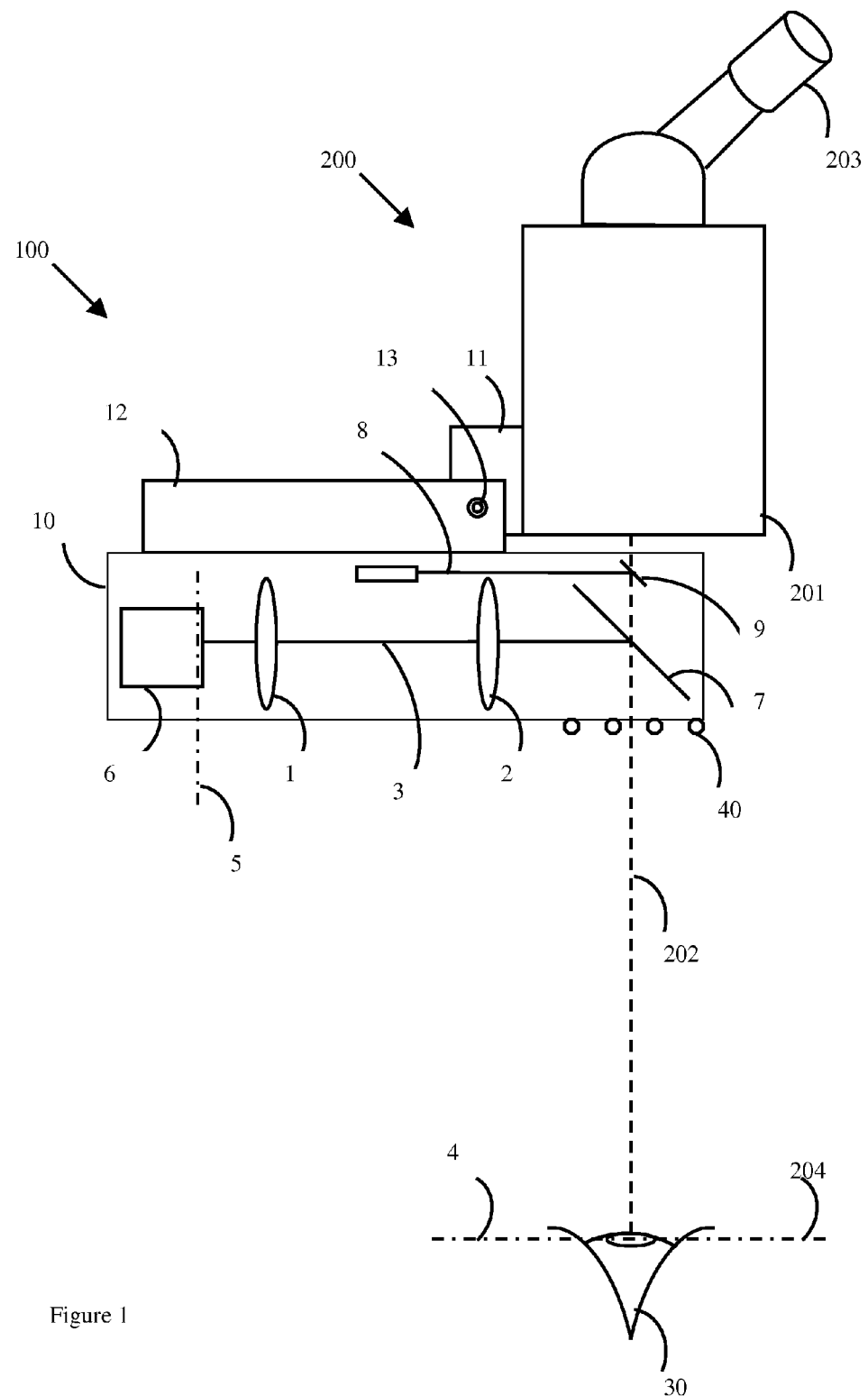
FIG. 1 shows an embodiment of a wavefront aberrometer attachable to an ophthalmic microscope.

FIG. 1 shows an embodiment of a wavefront aberrometer 100 attachable to an ophthalmic microscope 200. FIG. 1 is a side view of the ophthalmic microscope 200, which includes a microscope body 201, a left eyepiece 203, and a right eyepiece, which is not shown. The ophthalmic microscope 200 has a left viewing path and a right viewing path around the microscope's observation axis 202. The microscope 200 has an observation plane 204 predetermined with respect to the microscope body 201. The ophthalmic microscope 200 is movable via a positioning mechanism, which is not shown in the figure.

The microscope-attachable wavefront aberrometer 100 includes a first lens 1, a second lens 2, a wavefront sensor 6, a folding reflector 7, a probe beam 8, a turning mirror 9, an enclosure 10, a mounting block 11, an arm piece 12, and a mounting pin 13. The aberrometer 100 shall have physical dimensions comparable to or smaller than the ophthalmic microscope 200. The aberrometer 100 shall also have a weight substantially lighter than the ophthalmic microscope 200.

The first lens 1 and the second lens 2 form an afocal relay, which defines an optical axis 3, a front object plane 4, and a back image plane 5. The back image plane 5 is conjugated with the front object plane 4. The wavefront sensor 6 is placed at the back image plane 5 and is capable of receiving and measuring the wavefront aberration of a beam emerging from the object plane 4 and propagating through the afocal relay via the folding reflector 7. The design parameters for the optical afocal relay and wavefront sensor 6 are known to those skilled in the art.

The probe beam 8 is reflected via the turning mirror 9 to propagate along the observation axis 202. The probe beam 8 shall have a wavelength at the near infrared spectrum, ranging from 780 nm to 830 nm. The turning mirror 9 shall be small enough to place between the left viewing path and the right viewing path of the ophthalmic microscope. The probe beam 8 shall have a small vergence and a small spot size at the object plane 4. The probe beam 8 is projected into subject eye 30 to generate an emerging beam from the eye 30 to be measured. The design specifications for the probe beam 8 are known to those skilled in the art.

Depending on the working distance and the measurement range of optical power, the folding reflector 7 may have an aperture smaller or larger than the separation between the left and right observation paths of the microscope 200. When the aperture needs to be bigger than the separation between the left and right observation paths, the reflector 7 can be a thin dichroic mirror reflecting the probe beam 8 at near IR and transmitting visible light for microscope viewing.

The wavefront aberrometer 100 may further include a plurality of illuminators 40 disposed along a ring centered with the folded optical axis 202. The plurality of illuminators 40 can be made of an array of LEDs operated at infrared wavelength. The corneal reflection of the plurality of illuminators 40 can be employed for keratometry to measure the radius/radii of curvature of the subject cornea. It is helpful to measure the corneal power prior to an intraoperative aberrometer measurement. This way, the surgeon can avoid any cornea-induced wavefront error, such as corneal power change due to a change in intraocular pressure. On the other hand, should the keratometric readings be slightly different than preoperatively or as expected by the surgeon's technique, the differential values can be included in the calculation of the wavefront error by the software. The design concept and detection algorithm of a keratometer are known to those skilled in the art.

Another application of the plurality of illuminators 40 is to observe or measure the alignment of intraocular elements via the so-called Purkinje images I, III and IV. The design concepts and the use of Purkinje images I, III and IV are known to those skilled in the art. (If IR keratometry LEDs, than how to see Purkinje images?)

The plurality of illuminators 40 can be replaced with a Placido illuminator or other patterned spot illuminator. This way, corneal topography can be obtained via Placido image or patterned spot image. Corneal topographers can be useful for measurement of the corneal power and profile. The design concepts and the implementation of corneal topographers are known to those skilled in the art.

Figure 2:
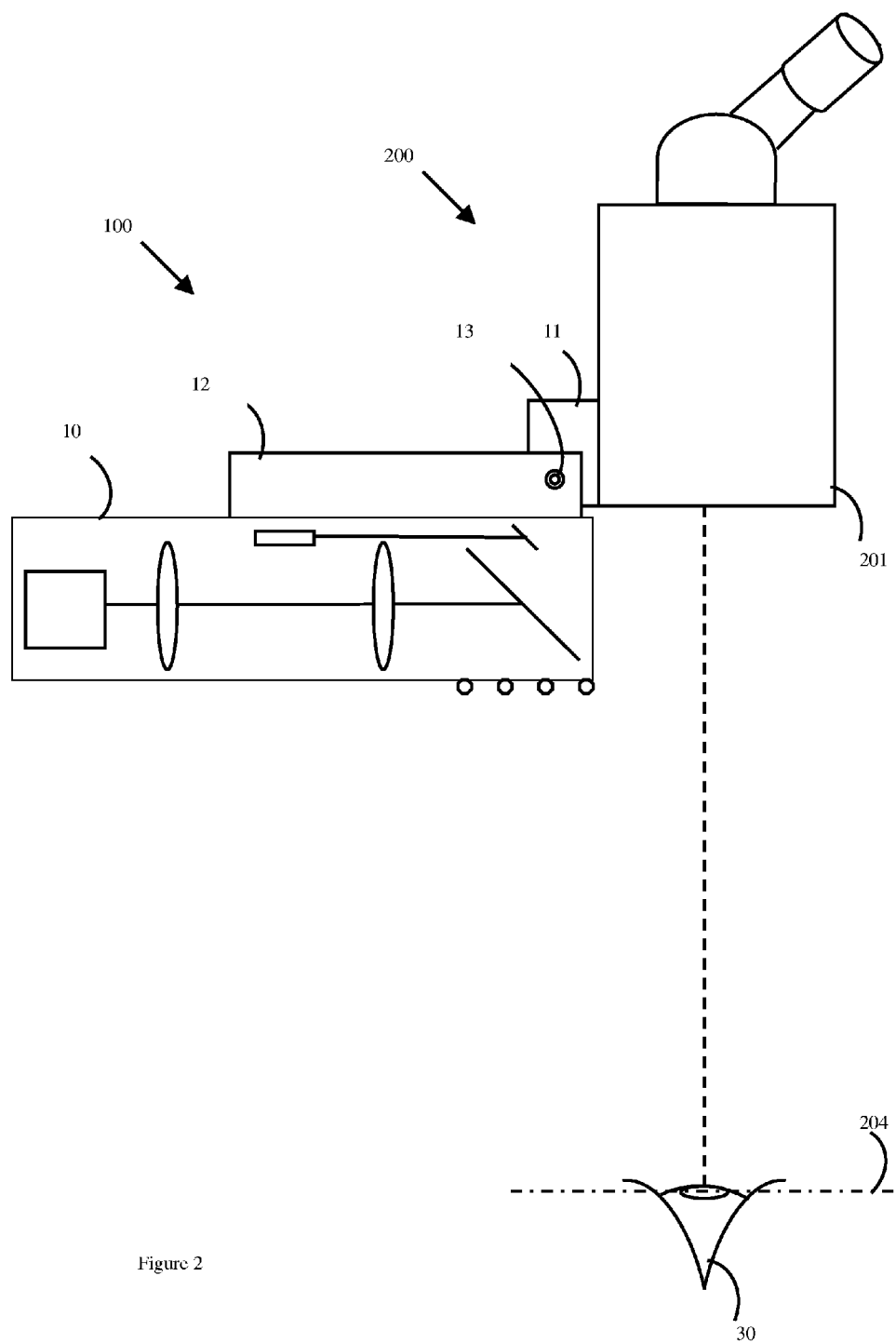
FIG. 2 shows an embodiment that a wavefront aberrometer is slid away from its working position.

FIG. 2 shows an embodiment whereby the wavefront aberrometer 100 is slid away from its working position. In this embodiment, a sliding mechanism between the enclosure 10 and the arm piece 12 enables the wavefront aberrometer to slide away from its working position. This way, the microscope-attachable aberrometer takes no space from the surgical microscope 200 when eye surgery is taking place. The sliding mechanism can be adapted from a number of sliding mechanisms known in the art.

Figure 3:
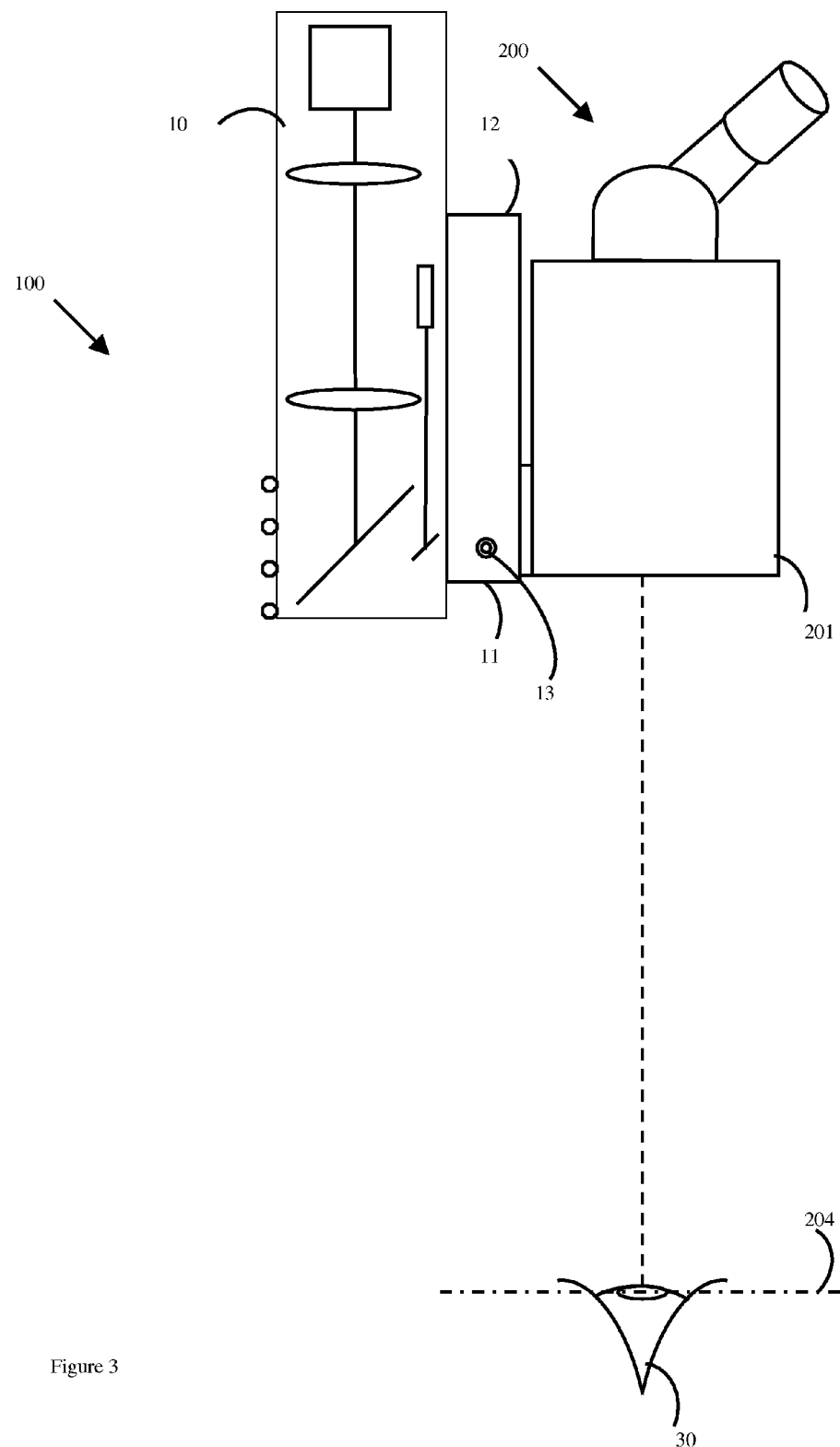
FIG. 3 shows an embodiment of a wavefront aberrometer that is slid away from its working position and further folded to clear working space for the ophthalmic microscope.

FIG. 3 shows an embodiment whereby the wavefront aberrometer 100 is slid away from its working position and further folded to clear working space for the surgical microscope 200. The sliding and folding mechanism can be adapted from a number of mechanisms known in the art.

Figure 4:
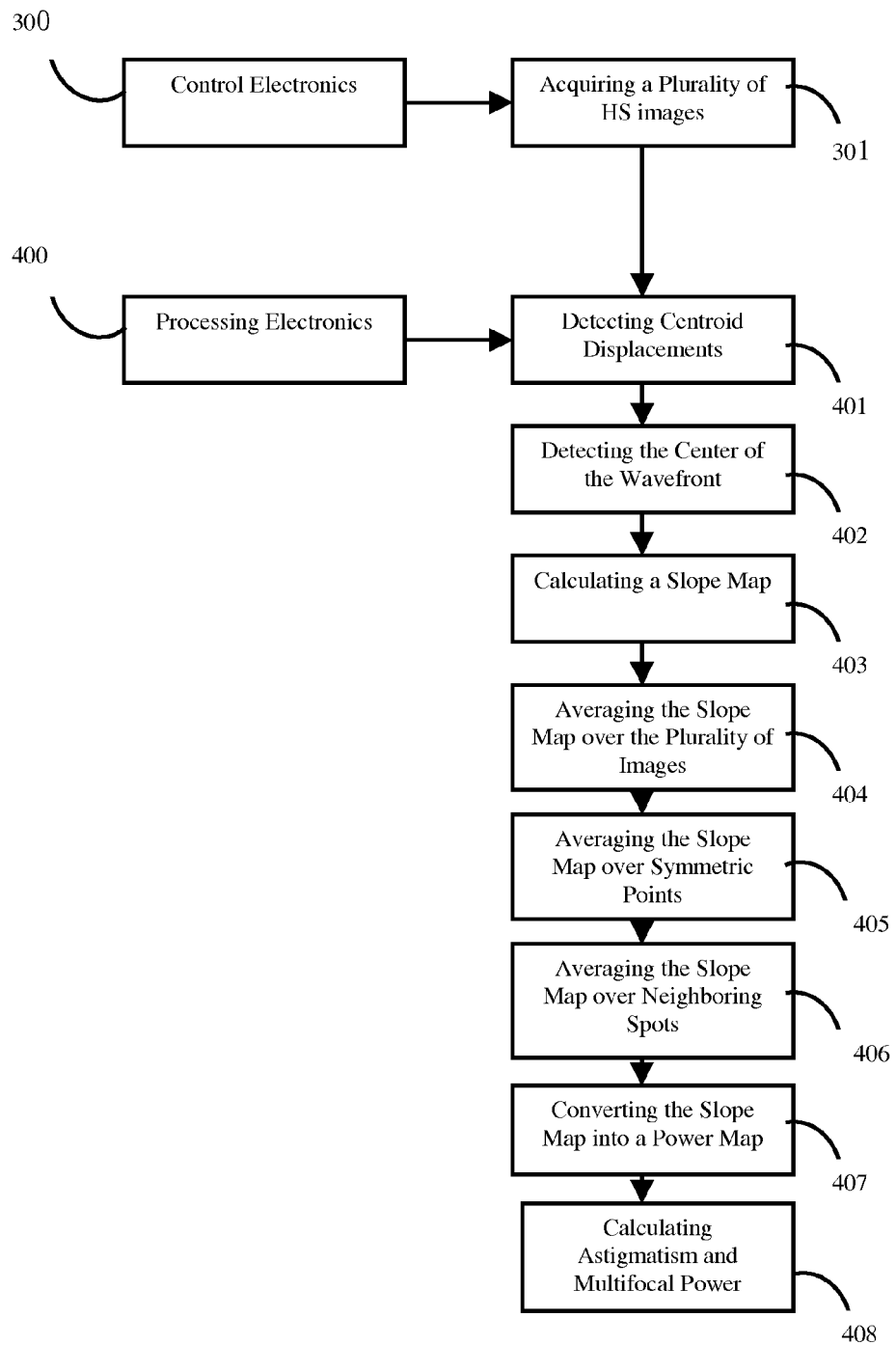
FIG. 4 shows control electronics and processing electronics implemented to measure optical power and astigmatism of a subject's eye that has been implanted with a multifocal IOL.

FIG. 4 shows control electronics 300 and processing electronics 400 implemented to measure optical power and astigmatism of the subject's eye implanted with a multifocal IOL. Control electronics 300 and processing electronics 400 can be incorporated with the wavefront aberrometer 100 to achieve these and other measurements.

It is well known in the art that a Hartmann-Shack wavefront aberrometer measures wavefront distortion via an image of Hartmann-Shack spots, in which the centroid of each spot represents a measurement data point. A collimated beam forms typically a regular-grid pattern of Hartmann-Shack spots and this spot pattern of the collimated beam can be used as a reference spot pattern of the aberrometer. A wavefront emerging from the subject eye 30 generates a spot pattern deviating from the reference spot pattern, and the deviations, i.e., the centroid displacements from their reference positions, can be used to determined the slope profile of the wavefront and thus to measure the optical power distribution of the eye.

Although a Hartmann-Shack spot pattern has typically 100 to 1000 spots, the spacing between the neighboring spots represents a limited spatial resolution of about 100 to 500 microns. Conventional Hartmann-Shack wavefront aberrometers employ a mathematical fitting technique to reconstruct the wavefront, assuming the wavefront a smooth and continuous surface. This fitting and reconstruction technique eliminates optical power change in a spatial scale comparable to the spot spacing, and consequently conventional Hartmann-Shack wavefront aberrometers are not useful in measuring multifocal IOLs having a transition zone typically on a scale of 100 microns.

Also, each Hartmann-Shack spot is subject to a rather large measurement uncertainty due to various spot distortions, stray lights, speckles, and poor signal to noise ratio. Fitting the spot pattern to a smooth wavefront surface is a powerful mathematical technique to remove the large measurement uncertainty of each Hartmann-Shack spot. However, this powerful technique is at a price as it reduces the spatial resolution of the optical power distribution and is thus not employed in the present invention for multifocal measurement.

The control electronics 300 is to acquire a plurality of Hartmann-Shack images in a single measurement, of which each image has a pattern of Hartmann-Shack spots. This plurality of Hartmann-Shack images are subsequently used to provide a much larger number of data points and to reduce the measurement uncertainty of the optical power distribution via statistical averaging instead of data fitting. Various mathematical techniques for data averaging of these kinds are known to those skilled in the art.

The processing electronics 400 is to measure the optical power distribution and to obtain a measurement with a precision acceptable for intraoperative application in cataract surgery, i.e., better than 0.25 D. As shown in FIG. 4, the processing electronics 400 includes a number of analysis circuits or calculation steps. A first algorithm 401 is to detect the centroid displacements of the Hartmann-Shack spots. A second algorithm 402 is to detect the center of the wavefront, based on the Hartmann-Shack image or other image of the eye. A third algorithm 403 is to employ the centroid displacements to calculate a slope map of the wavefront with respect to the center of the wavefront. A fourth algorithm 404 is to average the slope maps over the plurality of the Hartmann-Shack images. A fifth algorithm 407 is to convert the slope map into the optical power map. Finally, a sixth algorithm 408 is to calculate the multifocal power of the subject's eye from the optical power map.

Also shown in FIG. 4, the processing electronics 400 may further include an algorithm 405 to average each point in the slope map over its symmetric points. The processing electronics 400 may even further include an algorithm 406 to average each point in the slope map over its neighboring points.

Practically, 10 to 100 Hartmann-Shack images are acquired in a single measurement. Data averaging over the plurality of Hartmann-Shack images can be made with registering the center of each wavefront, e.g., a gravity center of each image of Hartmann-Shack spots. The averaging may be applied at various stages of data processing, e.g., centroid displacement map, slope map, or optical power map.

It is understood that the present disclosure includes only a few preferred embodiments and other modifications and variations may be made without departing from the following claims.

The invention claimed is:

1. A multifocal capable ophthalmic aberrometer, comprising:
    an afocal relay defining an optical axis, an object plane, and an image plane, wherein said image plane is conjugated to said object plane;
    a probe beam projected along said optical axis and propagating toward said object plane, wherein reflection of said probe beam from a subject eye located at said object plane generates a wavefront emerging from said object plane;
    a Hartmann-Shack sensor positioned at said image plane and producing an image of Hartmann-Shack spots of said wavefront;
    a control electronics acquiring a plurality of said images of said Hartmann-Shack spots in a single measurement; and
    a processing electronics calculating an optical power map of said subject eye with respect to a center of said wavefront and averaging said optical power map over said plurality of said images, wherein said processing electronics comprises:
        a first algorithm detecting the centroid displacements of said Hartmann-Shack spots;
        a second algorithm detecting a center of said wavefront;
        a third algorithm employing said centroid displacements to calculate a slope map of said wavefront with respect to said center of said wavefront;
        a fourth algorithm averaging said slope map over said plurality of said images;

a fifth algorithm converting said slope map into said optical power map; and a sixth algorithm calculating from said optical power map the multifocal power of said subject eye.

2. An ophthalmic aberrometer of claim 1, wherein said wavefront includes the feature of a multifocal lens.

3. An ophthalmic aberrometer of claim 1, wherein said wavefront includes the feature of a cylindrical lens.

4. An ophthalmic aberrometer of claim 1, wherein said wavefront includes the feature of an aspherical lens.

5. An ophthalmic aberrometer of claim 1, wherein said processing electronics further comprises:

an algorithm averaging each data point on said slope map over data points symmetric to said center of said wavefront.

6. An ophthalmic aberrometer of claim 1, wherein said processing electronics further comprises:

an algorithm averaging each data point on said slope map over data points around said each data point.

7. An ophthalmic aberrometer of claim 1, wherein said plurality of said images consists of 10 to 100 Hartmann-Shack images.

8. An ophthalmic aberrometer of claim 1, wherein said center of said wavefront is a gravity center of each image of said Hartmann-Shack spots.

9. A multifocal capable ophthalmic aberrometer, comprising:

an afocal relay defining an optical axis, an object plane, and an image plane, wherein said image plane is conjugated to said object plane;

a probe beam projected along said optical axis and propagating toward said object plane, wherein reflection of said probe beam from a subject eye located at said object plane generates a wavefront emerging from said object plane;

a Hartmann-Shack sensor positioned at said image plane and producing an image of Hartmann-Shack spots, of said wavefront;

a control electronics acquiring a plurality of said images of said Hartmann-Shack spots in a single measurement; and a processing electronics calculating a slope map of said wavefront with respect to a center of said wavefront, averaging said slope map over said plurality of said images, and converting said slope map into an optical power map of said subject eye, wherein said processing electronics comprises:

a first algorithm detecting the centroid displacements of said Hartmann-Shack spots;

a second algorithm detecting a center of said wavefront;

a third algorithm employing said centroid displacements to calculate a slope map of said wavefront with respect to said center of said wavefront;

a fourth algorithm averaging said slope map over said plurality of said images;

a fifth algorithm converting said slope map into said optical power map; and a sixth algorithm calculating from said optical power map the multifocal power of said subject eye.

10. An ophthalmic aberrometer of claim 9, wherein said wavefront includes the feature of a multifocal lens.

11. An ophthalmic aberrometer of claim 9, wherein said wavefront includes the feature of a cylindrical lens.

12. An ophthalmic aberrometer of claim 9, wherein said wavefront includes the feature of an aspherical lens.

13. An ophthalmic aberrometer of claim 9, wherein said processing electronics further comprises:

an algorithm averaging each data point on said slope map over data points symmetric to said center of said wavefront.

14. An ophthalmic aberrometer of claim 9, wherein said processing electronics further comprises:

an algorithm averaging each data point on said slope map over data points around said each data point.

15. A method for determining the optical power of a subject eye implanted with a multifocal intraocular lens, comprising the steps of:

providing an afocal relay defining an optical axis, an object plane, and an image plane, wherein said image plane is conjugated to said object plane;

projecting a probe beam along said optical axis and toward said object plane, wherein reflection of said probe beam from a subject eye located at said object plane generates a wavefront emerging from said object plane;

positioning a Hartmann-Shack sensor at said image plane to produce an image of Hartmann-Shack spots of said wavefront;

acquiring a plurality of said images of said Hartmann-Shack spots in a single measurement;

providing a first algorithm detecting centroid displacements of said Hartmann-Shack spots;

providing a second algorithm detecting a center of said wavefront;

providing a third algorithm calculating a slope map of said wavefront with respect to a center of said wavefront;

providing a fourth algorithm averaging said slope map over said plurality of said image; and providing a fifth algorithm converting said slope map into an optical power map of said subject eye;

providing a sixth algorithm calculating from said optical power map a multifocal power of said subject eye.

16. A method of claim 15, further comprising the steps of:

averaging each data point on said slope map over data points symmetric to said center of said wavefront.

17. A method of claim 15, further comprising the steps of:

averaging each data point on said slope map over data points around said each data point.

18. A method of claim 15, wherein said wavefront includes the feature of a multifocal lens.

19. A method of claim 15, wherein said wavefront includes the feature of a cylindrical lens.

20. A method of claim 15, wherein said wavefront includes the feature of an aspherical lens.

* * * * *